Dec. 18, 1951 P. ECKE Plant Pat. 1,055
POINSETTIA PLANT
Filed May 25, 1950
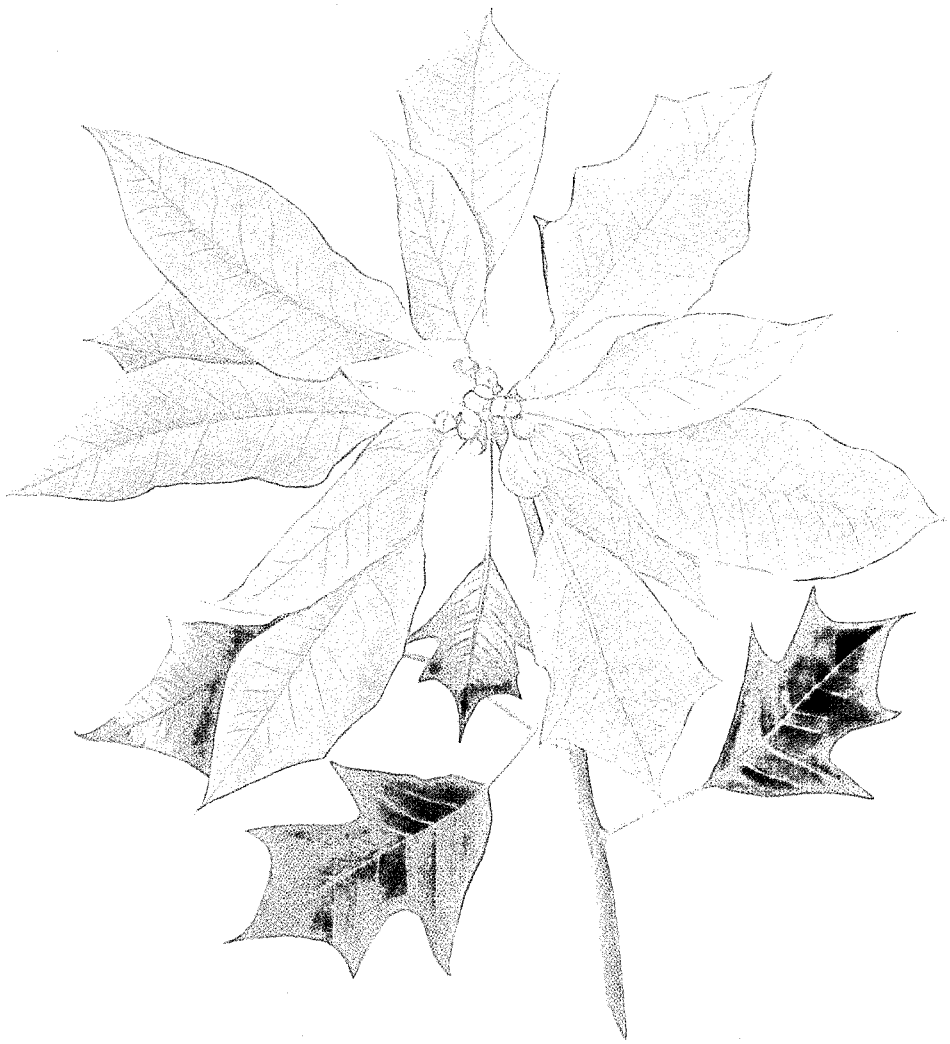
INVENTOR
PAUL ECKE
By Jas. S. Graham
Attorney Patented Dec. 18, 1951

Plant Pat. 1,055

UNITED STATES PATENT OFFICE 1,055

POINSETTIA PLANT

Paul Ecke, Encinitas, Calif.

Application May 25, 1950, Serial No. 164,129

1 Claim. (Cl. 47—60)

The present discovery relates to a new and distinct variety of poinsettia plant (*Euphorbia pulcherrima*), originating as a sport.

Broadly, this new variety of poinsettia plant is distinguishable from the parent plant, as well as from other known varieties, mainly by the shape, color and subcoriaceous character of bracts and foliage leaves, and the tenacity of holding the foliage on the peduncle. More specifically, it is also distinguishable from other known varieties by the arrangement of the individual character of the bracts which are relatively long, wide and few in number and a majority of which are mounted on comparatively long petioles, so that the bract involucre is open at its center around the inflorescence.

The accompanying illustration, forming a part of this application, graphically shows in color the subject in its full maturity, the illustration being a face view of the subject, shown in its normal condition, with its grace and charm of appearance.

The colors mentioned herein correspond approximately with those shown in "Horticultural Color Chart," issued by The British Colour Council in Collaboration with The Royal Horticultural Society, and identified by the color name and plate of said color standard by recapitulation in tabular form.

The following is a detailed description of this new variety.

*Parentage*

In the summer of 1945 a sport of poinsettia plant of my Plant Patent No. 242 of April 6, 1937, was discovered by me on one of my poinsettias of the aforesaid patented variety, in glassed house at Encinitas, California, and has been asexually reproduced by cuttings. It has remained true to type and the herein described characteristics through the propagation of several thousand plants over a period of more than four years, and has shown its qualities and characteristics to be permanently fixed.

*Structure*

The peduncles which branch from the main trunk are scheeles green and are long, stiff, and very strong. They are comparatively small in cross-section. Their average length is four feet, with several small pedicels at the top usually growing as knob-like spurs each of which bears a few sub-acaulescent flowers. From the knob-like spurs also grows an involucre of bracts.

*Petioles*

Extending outwardly from around each of the peduncles is a plurality of foliage leaves the petioles of which are attached to and arranged helically around the peduncle, their color being cherry.

*Foliage leaves*

The foliage leaves are arranged alternately helically on the peduncle. The shape of the leaf is oakleaf type, and very prominently and deeply pinnatifid or paripinnate, the teeth being acuminate. The leaf is thick and subcoriaceous, at optimum of maturity the three or four foliage leaves most nearly adjacent the bracts become irregularly variegated in colors of delft rose to spinach green, and those more remotely positioned becomes a substantially uniformly spinach green color. The leaves are tenacious in holding to the peduncle for a period of from ten to twenty days longer than the older types of poinsettias such as commonly known as the St. Louis variety which applicant believes has been known by that name since about 1929, and is not a patented variety.

*Bracts*

The bracts, in planar contour are elongated and a portion of them are ovate-acuminate while another portion are ovate and modified pinnatifid, though not as prominently or deeply pinnatifid as the foliage leaves. The bracts are definitely subcoriaceous. At the optimum of their maturity the bracts and their petioles are of cardinal red color, and maintain a uniformity of color in a wider differential range of temperatures than known varieties of poinsettia.

The bracts are further characterized by a numerically less number of individual bracts than known varieties of poinsettia, such as my Plant Patents Nos. 242, 336 and 343, but the predominating majority of individual bracts are of greater axial length and greater transverse width and greater individual planar area, than known varieties. Further, the petioles of the predominating majority of individual bracts are uncommonly elongated, which, together with the axial length of the bracts, extends the bracts radially so that the mean diameter of the involucre is greater than the linear distance between apices of relatively oppositely disposed foliage leaves adjacently therebelow. The phenomena thus present provides an involucre of bracts openly spaced at the center around the inflorescence, and the contour of the separate bracts is individually emphasized.

*Inflorescence*

A node is formed on the upper end of each peduncle, each of which usually presents three short and comparatively large heavy stem-like knobs or spurs, which protrude upward and expansively apart, each knob or spur providing the base for a plurality of short subacaulescent stems, and each stem terminating in a flower the perianthial calyx of which, prior to maturity is substantially white, and which at maturity is of a scheeles green color. Each of the flowers usually develops three ovules in a nectar cup of chrome yellow at substantially the center of which is a pistil of cardinal red color, substantially similar to the color of the bracts.

*Dimensions*

The total height of the plant at maturity, including main trunk and peduncles, is approximately eight feet, and the greatest lateral dimension is approximately five feet.

*Habits of growth*

Vigorous, but slow in growth, easily cultivated, if properly handled, and persistent and perennial in growth. Foliage, bracts and inflorescence occur annually, maturing in Southern California from November to December, the optimum elsewhere being modified by climate and growing conditions.

*Immunity*

The entire plant seems to be immune or highly resistant to insects, disease, and all other obnoxious and detrimental interference.

*Variations*

Different plants of this new variety have an unusual similarity of adherence to characteristics and type. However, in comparison with the same grown in various localities, in different soil, and at various times of the year, in different temperature, or in different greenhouses or in the open, and even by different persons, there may be slight variations of minor detail.

*Propagation*

Propagation is by cuttings planted at any time from May until September, and the plant will mature to optimum from November to December, retaining bracts and foliage for substantially two months, after which the plant will remain dormant for about three months.

*Colors*

The color designations according to the color plates of said Horticultural Color Chart are recapitulated in tabular form as follows:

| Element | Color | Sheet | Plate |
|---|---|---|---|
| Peduncle | Scheeles green | 175 | 860/2 |
| Petioles | Cherry | 157 | 722/2 |
| Foliage Leaves: | | | |
| Those adjacent bracts, Variegated. | Delft Rose to Spinach green | 108 to 108 | o20/3 o20 |
| | | 187 to 187 | o960 o960/1 |
| Those more remote from bracts. | Spinach green | 187 | o960 |
| Bracts | Cardinal red | 168 | 822/1 |
| Inflorescence: | | | |
| Calyx | Scheeles green | 175 | 860/3 |
| Nectar cup | Chrome Yellow | 144 | 605 |
| Pistil | Cardinal Red | 168 | 822/1 |

Having described and illustrated my new variety of poinsettia plant, I claim:

A new and distinct variety of poinsettia plant substantially as illustrated and described, characterized by cardinal red subcoriaceous bracts which are ovate-acuminate, the bracts having petioles sufficiently long to provide an open spaced center of the bract involucre and whereby the contours of the bracts are individually in planar profile around the inflorescence, the foliage leaves being also subcoriaceous and deeply pinnatifid and tenaciously adhering to the peduncle, the several foliage leaves most nearly adjacent the bracts being variegated with shades of rose to green.

PAUL ECKE.

No references cited.